(12) United States Patent
Schroeder et al.

(10) Patent No.: US 8,307,832 B2
(45) Date of Patent: *Nov. 13, 2012

(54) METHOD AND DEVICE FOR INCREASING AN OPTICAL SYSTEM FOCAL DEPTH

(75) Inventors: Eckhard Schroeder, Eckental (DE); Matthias Wottke, Burgthann (DE); Rudolf von Buenau, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/117,221

(22) Filed: May 27, 2011

(65) Prior Publication Data

US 2011/0228217 A1 Sep. 22, 2011

Related U.S. Application Data

(63) Continuation of application No. 11/909,444, filed as application No. PCT/EP2006/002692 on Mar. 23, 2006, now Pat. No. 7,950,398.

(30) Foreign Application Priority Data

Mar. 23, 2005 (DE) .................... 10 2005 013 558

(51) Int. Cl.
*A61B 19/00* (2006.01)

(52) U.S. Cl. .......................................... 128/898; 606/5
(58) Field of Classification Search .......... 351/205–212; 606/4, 5, 10–12, 166; 128/898
See application file for complete search history.

(56) References Cited

U.S. PATENT DOCUMENTS

| | | | |
|---|---|---|---|
| 5,777,719 A | 7/1998 | Williams et al. | |
| 6,099,522 A | 8/2000 | Knopp et al. | |
| 6,923,802 B2 | 8/2005 | Williams et al. | |
| 7,261,412 B2 | 8/2007 | Somani et al. | |
| 7,950,398 B2 * | 5/2011 | Schroeder et al. | 128/898 |
| 2001/0041884 A1 | 11/2001 | Frey et al. | |
| 2004/0169820 A1 | 9/2004 | Dai et al. | |

FOREIGN PATENT DOCUMENTS

| | | |
|---|---|---|
| DE | 10022995 A1 | 11/2001 |
| WO | WO 2004/052253 | 6/2004 |
| WO | WO 2006/056847 | 6/2006 |

* cited by examiner

*Primary Examiner* — Ahmed Farah
(74) *Attorney, Agent, or Firm* — Leydig, Voit & Mayer, Ltd.

(57) ABSTRACT

A method for changing a property of an eye uses a continuously multifocal profile that includes a component for increasing a focal depth. The method includes calculating the component for increasing the focal depth to be rotation-symmetrical. Alternatively, or in addition, the calculating is carried out so as to optimize an encircled energy criterion over an extended range of depth.

10 Claims, 2 Drawing Sheets

METHOD AND DEVICE FOR INCREASING AN OPTICAL SYSTEM FOCAL DEPTH

CROSS REFERENCE TO RELATED APPLICATIONS

This is a Continuation application of U.S. patent application Ser. No. 11/909,444, filed Sep. 21, 2007, which issued as U.S. Pat. No. 7,950,398 on May 31, 2011, which is the U.S. National Phase application under 35 U.S.C. §371 of International Application No. PCT/EP2006/002692, filed Mar. 23, 2006 and claims the benefit of German Patent Application No. 10 2005 013 558.7, filed on Mar. 23, 2005. The International Application was published in German on Sep. 28, 2006 as WO 2006/100086 under PCT Article 21 (2).

FIELD

The invention relates to a method for changing the properties of an optical system by means of a continuously multifocal profile.

BACKGROUND

International patent application WO 2004/052253 A1 describes an excimer laser unit and a corresponding control method for performing a corneal ablation to reduce presbyopia. Here, the excimer laser unit is controlled in such a way that, through the ablation of the cornea, a slightly positive fourth-order spherical aberration (Z(4.0)) is created in the cornea. The loss of the power of accommodation of the eye caused by presbyopia is at least partially compensated for by the increase in the spherical aberration of the eye thus achieved. By incorporating a positive fourth-order spherical aberration, a considerable improvement in near vision can be achieved, especially in the case of presbyopia.

However, it has been found that, by incorporating a spherical aberration of the type described in WO 2004/052253 A1, the base refraction of the eye is changed. This results in a deterioration of the distance vision or far vision. Consequently, with the known method, creating a fourth-order aberration achieves an improvement of the near vision in cases of presbyopia, but this comes "at the expense of" the distance vision.

SUMMARY OF THE INVENTION

It is an object of the present invention is to propose a method and an appertaining device with which an increase in the focal depth of an optical system can be achieved that leads to an improvement in the near vision without an associated deterioration of the distance vision. An increase in the focal depth is to be achieved that is refraction-neutral for the distance vision.

The present invention provides a method for changing the properties of an optical system by means of a continuously multifocal profile including a component for increasing a focal depth. The method includes calculating the component for increasing the focal depth to be rotation-symmetrical. Alternatively, or in addition, the calculating is carried out so as to optimize an encircled energy criterion over an extended range of depth.

The optical system according to the invention is preferably an eye. In this case, the continuously multifocal profile can preferably be in the form of an ablation on the surface of the cornea of the eye. Instead of an ablation of the cornea, however, an appropriate change can be made in the contour of contact lenses or intraocular lenses. With intraocular lenses, instead of a contour change, a change in the volume refractive index is also conceivable, which can lead to corresponding changes in the image-forming properties. This change in the volume refractive index is especially preferably done so as to vary along the lens so that the lens has areas with predefined volume refractive indices that differ from each other. In this manner, the refractive index of the lens rather than the shape is changed in a targeted manner. Therefore, if the optical system is a contact lens or an intraocular lens, then an artificial lens is treated rather than the eye itself.

The ablation of the surface of the object to be treated, that is to say, the cornea, the contact lens or the intraocular lens, or the change in the refractive index is done according to a calculated profile. This profile indicates where and how the surface of the object to be treated is to be ablated or where and how the refractive index is to be changed. According to the invention, the profile can be represented by a sum of Zernike polynomials. Here, different constituents of the sum, that is to say, different Zernike polynomials or combinations of Zernike polynomials, form different components of the ablation profile. Thus, different types of corrections to the optical system can be achieved with different Zernike polynomials present in the sum.

According to the invention, the profile comprises at least one component for improving the focal depth of the optical system. The focal depth can also be referred to as depth of field or range of focus. This refers to the extension of the sharply defined area in the direction of the optical axis of the optical system. In the case of an eye, the depth of field is the distance range within which the eye can see "sharply" at a given focus. An increase in the focal depth can counter the presbyopia which is characterized in that the power of accommodation of the eye diminishes.

In fact, in presbyopia, especially the capability of near accommodation diminishes. This means that a presbyopic eye is no longer capable of seeing sharply at a close range. Within a certain close range, focusing is no longer possible, so that objects at such a close range (e.g. text when reading a newspaper) are unsharp. If the focal depth of the eye in this close range, especially in the direction of the eye, has been improved by means of the method according to the invention, then near objects can continue to be perceived sharply even though the eye has lost its ability to focus at such a short range. Even though the object is "too close" to the eye and thus proper focusing is no longer possible, the object is nevertheless perceived sharply since it lies within the focal depth range that has been extended by means of the method according to the invention.

The inventive component of the profile for increasing the focal depth is formed on the basis of a fourth-order Zernike polynomial and additionally on the basis of a second-order Zernike polynomial. Therefore, in contrast to known methods, the invention proposes focusing not only a fourth-order Zernike polynomial but also a second-order Zernike polynomial in order to increase the focal depth. Adding a second-order polynomial precisely compensates for the change in the base refraction of the object to be ablated that is disadvantageously caused by the addition of a fourth-order Zernike polynomial. Therefore, with the addition according to the invention of another second-order term, the undesired side effects stemming from the introduction of a fourth-order term are eliminated. Thus, in cases of presbyopia, the near vision can be improved without the distance vision suffering from this. Consequently, one could also refer to the second-order term added according to the invention as a correction term that brings about a refraction-neutral compensation.

With the state of the art mentioned above, the introduction of a second-order Zernike polynomial is carried out at best in the well-known manner so as to compensate for nearsightedness or farsightedness (myopia or hyperopia). However, in contrast to the invention, an additional second-order term as part of a treatment to decrease presbyopia (with a correction through the introduction of a fourth-order Zernike polynomial) is not provided.

Especially preferably, the profile is generated by ablation. Such an ablation profile is known in ophthalmology in order to generate appropriate continuously multifocal profiles through the ablation of material from the surfaces of a lens of an optical system or of an eye, thereby bringing about a change in the refractive properties. In addition to an ablation of material, it is also conceivable to add material at certain places. In this manner, all kinds of optical elements in an optical system can be provided with an appropriate profile.

Moreover, it is preferred to generate the profile by changing the refractive index of the optical system, especially of a lens. In this way, it is possible to effectuate a change in the refractive properties of the optical system by systematically changing the refractive power, for example, by irradiating the material, without changing the dimensions of the object itself, as is the case with an ablation or an addition of material. Special preference is given to generating a profile through a combination of ablation on the one hand and a change in the refractive index of the optical system through irradiation and a change in the material properties on the other hand.

In order to achieve an even more precise improvement of the focal depth, the component for increasing the focal depth can additionally have a sixth-order and/or higher-order Zernike polynomial. The profile for increasing the focal depth can be further optimized by adding other higher-order polynomials. At this juncture, it should be taken into consideration that, like with the introduction of a fourth-order polynomial, the introduction of sixth-order and/or higher-order polynomials can cause undesired side effects. In a preferred embodiment, these efforts are compensated for by the addition of further, lower-order terms.

It is also conceivable that other Zernike polynomials such as, for example, Koma polynomials (third order) are also employed in order to generate a multifocality or in order to improve the focal depth.

Preferably, the component for increasing the focal depth is rotation-symmetrical. This means that the polynomials that make up the component are radial polynomials. Radial polynomials are polynomials that, in a polar notation, are characterized in that they do not have any angular dependence. Special preference is given to the use of a Z(2.0) term for the second-order Zernike polynomial, a Z(4.0) term for the fourth-order Zernike polynomial and a Z(6.0) term for the sixth-order Zernike polynomial.

If the optical system is an eye, the photopic and mesopic diameter of the pupil of the eye can additionally be taken into account for calculating the component for increasing the focal depth. The photopic diameter is the diameter of the pupil in daylight, whereas the mesopic diameter is the diameter of the pupil at dusk. By taking into account the fact that the diameter of the pupil of the eye varies under different light conditions, a better optimization of the profile can be achieved. If a profile optimized in such a way is used for ablation, the correction of the presbyopia is not made only for a defined pupil (light or dark) but rather, the correction is optimal under good as well as under poor light conditions.

If the different pupil diameters are to be taken into consideration, then preferably the extension of the profile is determined by the mesopic pupil diameter of the eye. Hence, the diameter of the pupil under mesopic light conditions forms the basis for the determination of the optical zone to be treated. In particular, this can mean that the diameter of the profile essentially corresponds to the ascertained mesopic pupil diameter.

If the optical system is an eye and if the photopic and mesopic diameters of the pupil of the eye are to be taken into consideration in order to ascertain the ablation profile, then this consideration can be carried out especially in that the ablation profile brings about a stronger refractive power in a central area of the optical system within the photopic diameter than in a peripheral, annular area between the photopic and mesopic diameters. Then, when used in the center of the object to be ablated within the photopic diameter, the ablation profile generates a greater refractive power than in the area around the center extending to the mesopic diameter. Due to the induced stronger refractive power, the central area is especially optimized for near vision, whereas the peripheral area is optimized for distance vision by the somewhat weaker refractive power that has been induced.

Especially preferably, the profile is even further augmented by transition zones at its edge. These transition zones are located around the effective optical zone, whereby the diameter of the effective optical zone—as already described—preferably corresponds to the diameter of the mesopic pupil. Through the addition of transition zones, the profile with the profile change to the edges caused by the use of the profile ensures a uniform transition. Thus, greater, abrupt and thus undesired angle changes in the ablated surface of the object to be treated are avoided.

It can also be provided that the coefficients of the Zernike polynomials for calculating the component for increasing the focal depth are selected in such a way that the encircled energy criterion is optimized over an extended range of depth. Here, it is especially advantageous if the diameter for the encircled energy criterion corresponds to the effective detector diameter of the optical system. The above-mentioned detector is preferably a photoreceptor cell on the retina.

This means that the coefficients of the polynomials are selected in such a way that, after the profile is used on the object to be ablated, the optical system was changed in such a way that, over an extended range of depth, a high percentage of the light beams from an object to be detected by the optical system are always focused within the effective detector diameter on the image plane of the optical system. Hence, if the optical system comprises an eye, and if the object to be ablated is the cornea of the eye, then the coefficients of the polynomials are selected in such a way that, when the resultant ablation profile is used on the cornea, objects detected by the eye in the area from the near vision to the distance vision of the eye are always focused so precisely on the retina of the eye (in the eye, the image plane is the retina) that an image is formed on the retina for each point of the detected object, and for said image, for example, at least 90% of the appertaining light beams are focused on the retina within a circle whose diameter is not larger than that of a photoreceptor cell on the retina.

Thus, if the coefficients are selected in such a way that "only" the encircled energy criterion is fulfilled, then after the ablation has been performed, no exact point focusing is achieved along the range of depth. However, this is not a drawback as long as the unsharpness is not greater than the diameter of a photoreceptor cell. In fact, a focusing that is more exact than the diameter of a photoreceptor cell cannot be detected by the photoreceptor cells of the retina anyway. By turning to the encircled energy criterion, the profile can thus be simplified or selected "more coarsely", without this reducing the quality of the correction that has been made.

Preferably, the profile additionally comprises a component for correcting myopia, hyperopia and/or astigmatism. In this case, the ablation profile serves not only to increase the focal depth of the optical system, but also to make a correction of the above-mentioned visual inadequacies. Therefore, the method according to the invention for correcting presbyopia can also be incorporated into a method for the correction of other visual inadequacies.

Especially preferably, a method is also provided with which—instead of or in addition to an ablation—a change in the refractive index of the optical system, especially of a lens, is also provided. In this manner, instead of a contour change, it is possible to make a change in the volume refractive index, which likewise leads to changes in the image-forming properties. Such a change in the volume refractive index is preferably configured to be continuously multifocal. Special preference is given to a combination of the ablation on the one hand and the change in the refractive index on the other hand. Especially preferably, the change in the refractive index is made to an intraocular lens—but it is also conceivable to make the change in the refractive index additionally or exclusively to other optical elements such as, for example, a contact lens, an eyeglass lens or the cornea.

Finally, in order to achieve the above-mentioned objective, the present invention also proposes a device for carrying out one of the methods described above.

Such a device preferably comprises a unit for generating a profile of an optical system, preferably comprising a control unit for a shaping unit, preferably a laser, especially an excimer laser or a femtosecond laser as well as a control unit for applying, for example, a laser beam or generally a radiation beam onto the object to be treated. Moreover, preferably a computing unit is provided for determining Zernike polynomials for increasing the focal depth. Especially preferably, an aberometer is also provided that can determine the actual state of the optical system and that can communicate or verify the progress of the modification of the optical system brought about through the change of the profile, especially preferably online.

DESCRIPTION OF PREFERRED EMBODIMENTS

The method according to the invention will now be explained with reference to FIG. 1.

A method for multifocal corneal surgery for the correction of presbyopia is described. This method for the correction of presbyopia can be performed in emmetropic eyes, i.e. in eyes that are exclusively presbyopic but that otherwise have normal vision, and also in shortsighted (myopic), farsighted (hyperopic) and/or astigmatic eyes that are additionally presbyopic.

Figure 1:
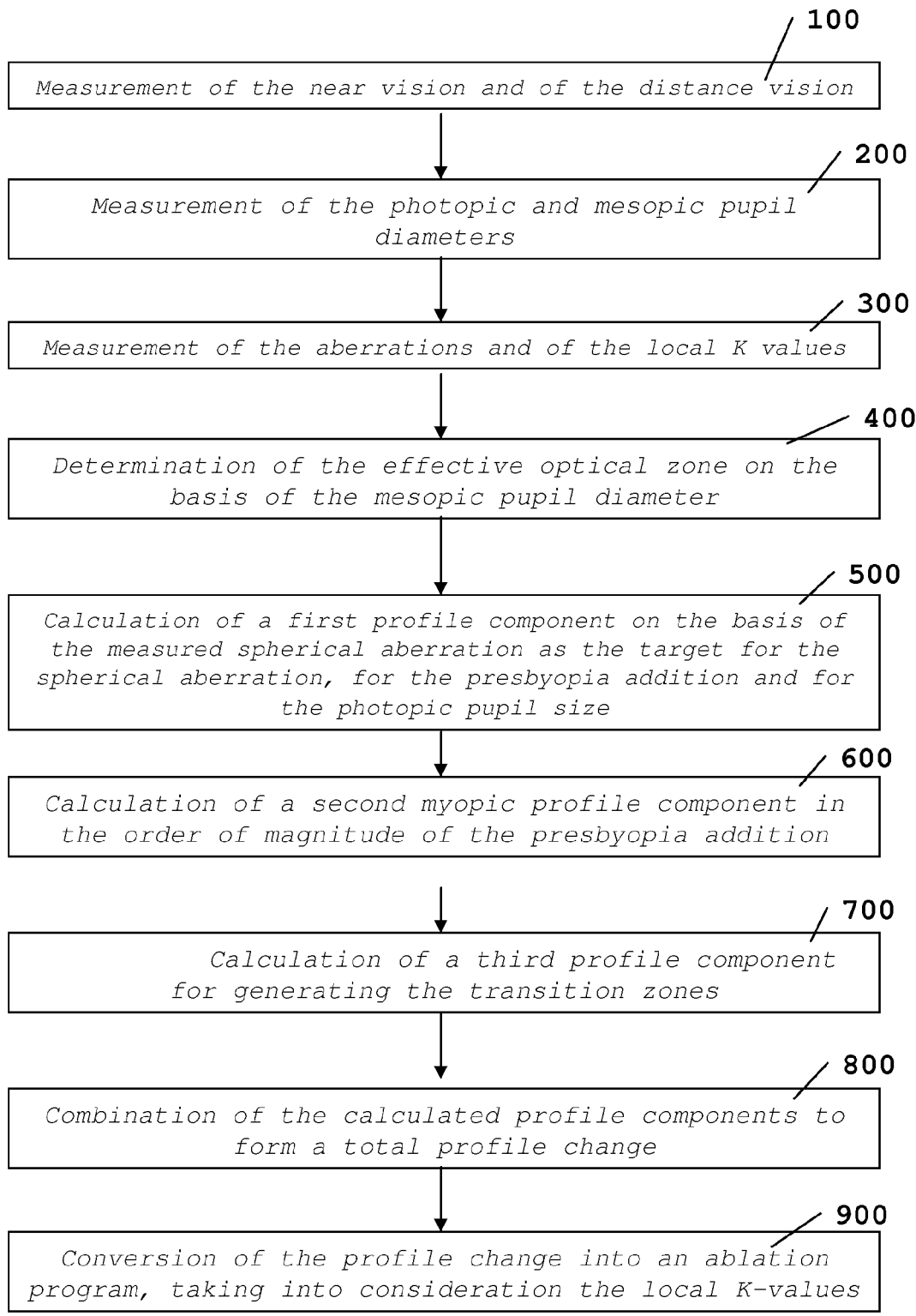
FIG. 1 shows a flow diagram that illustrates an embodiment of a method according to the invention.

At this juncture, it should be pointed out that the flow diagram according to FIG. 1 exclusively shows the method for emmetropic eyes. There are further method steps in the case of eyes with additional visual inadequacies.

As can be seen in FIG. 1, the method starts in that the near vision and the distance vision in the eye that is to be treated are measured (Step 100). Then the pupil size, i.e. the diameter of the pupil in daylight (photopic) as well as under dusk conditions (mesopic) is determined (Step 200). Then, if applicable, the values for a standard correction (sphere, cylinder, axis) are measured if corresponding "standard visual inadequacies" (myopia, hyperopia, astigmatism) are present. In order to correct the presbyopia, the higher aberrations and the K-values are measured (Step 300). Then, on the basis of the ascertained mesopic pupil, the optical zone of the treatment is determined (Step 400), the optical zone being the effective optical zone without a transition zone.

On the basis of the measurements taken, the profile change to be made to the cornea of the eye can now be calculated. In order to correct the presbyopia, a profile change is calculated that consists of two components. Here, to start with, a first profile component is calculated from the preoperative spherical aberration, from the presbyopia addition and from the daylight pupil as the target for the spherical aberration (Step 500). This first component exhibits a higher refractive power centrally in the range of the daylight pupil than in the range between the daylight pupil and the mesopic pupil. Here, the Zernike polynomials are used in order to calculate this first component. The first profile component is calculated from the Z(4.0), the Z(6.0) and possibly other higher-order Zernike polynomials.

In addition to the first component, however, a myopic component is needed, which compensates for the refractive change caused as an undesired side effect by the first component (Step 600). For this purpose, a Z(2.0) term in the order of magnitude of the presbyopia addition is employed.

The sum of the determined first and second components form the portion of the profile change that serves to correct the presbyopia.

Moreover, a third component for the profile change is also calculated (Step 700). This third component provides the transition zones at the edge of the profile change in order to avoid greater angle changes of the cornea surface.

Finally, if applicable, on the basis of the values for a standard correction, a fourth component is formed for correcting myopia, hyperopia and/or astigmatism.

The calculated profile components are finally combined to form a total profile change (Step 800). Then this total profile change—consisting of Z(2.0), Z(4.0), Z(6.0), a transition zone and, if applicable, a standard correction—is converted into an ablation program for an ablative excimer laser (Step 900). However, such a total profile change is only possible if the calculation or treatment diameter is selected to be the same for all of the components. However, it is also conceivable to dispense with the formation of a total profile change and to remain with a two-part treatment, for example, along the lines that the basic correction (myopia, hyperopia, astigmatism) is contained in one part and the presbyopia correction is in a second part with a different diameter.

Reasons for different diameters can be, for instance, that, due to insufficient corneal thickness, the basic correction in cases of severe visual inadequacies can only be carried out with a smaller diameter than the pupil diameter would require for the presbyopia portion.

Thus, greater variability of the surface is achieved, which can no longer be described only by Zernike polynomials up to the fourth order. During the conversion into an ablation program, the local K-value of the cornea is taken into account so that this ablation program does not induce any uncontrolled spherical aberrations.

Figure 2:
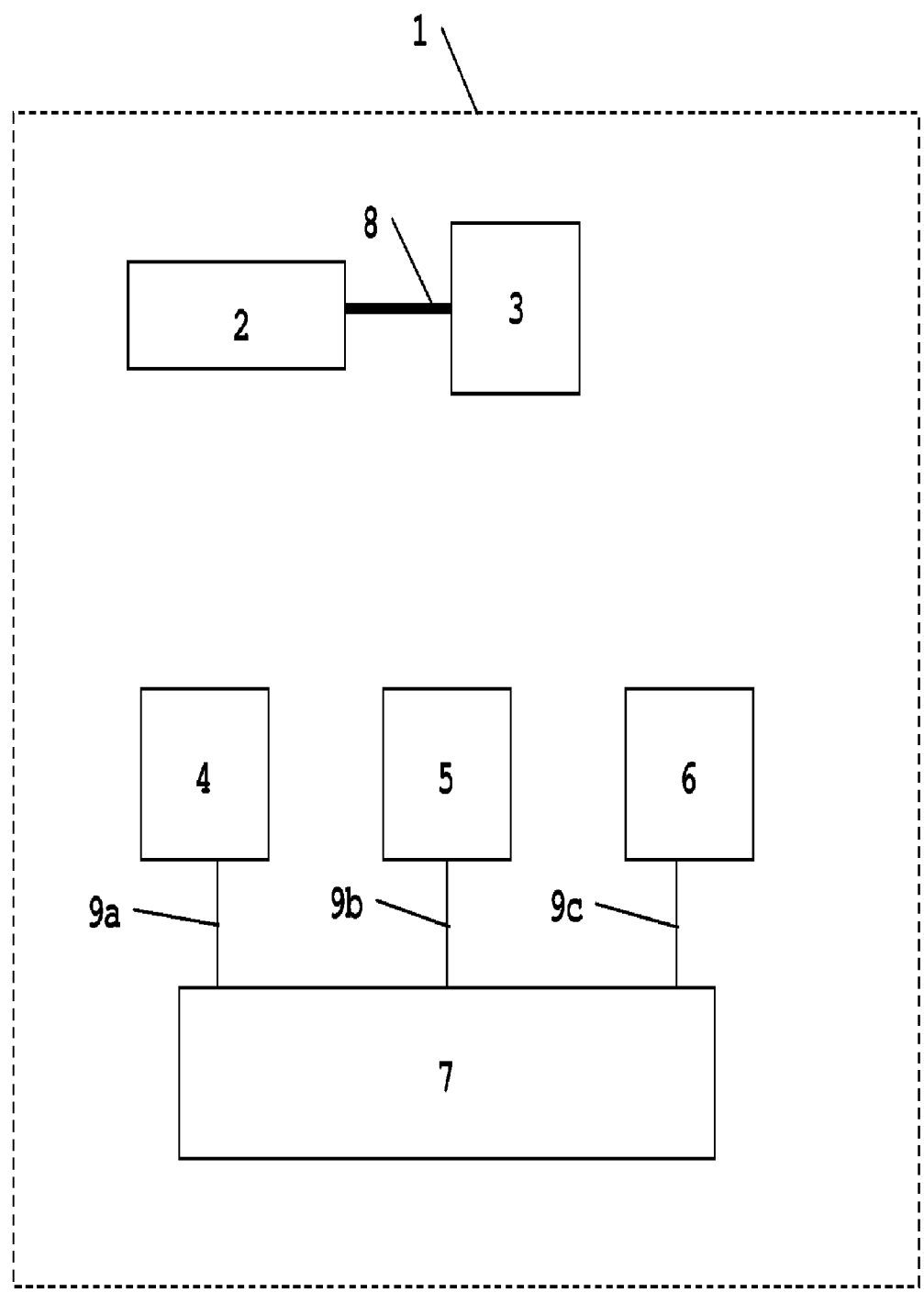
FIG. 2 shows an embodiment of a device according to the invention for carrying out a method according to the invention.

A device 1 for carrying out the method just described is presented on the basis of FIG. 2.

The device 1 comprises a light source or radiation source 2, a beam modification device 3, a wavefront analysis device 4, a topography analysis unit 5, a means 6 for measuring the photopic and mesopic pupil diameter and a means 7 for deriving a photo-ablation profile.

The radiation source 2 is preferably a laser, especially a refractive laser. As a rule, a spot scanning excimer laser system is provided as the radiation source 2. As an alternative, the laser can also be an fs-laser. The beam-forming and guide system 3 serves to form and deflect a beam 8 of the radiation source 2. In order to form the beam 8, the device 3 preferably has lens systems, diffractive or refractive micro-optical elements. In order to collimate and deflect the beam, the device 3 preferably has scanner arrays, prisms or mirrors.

The wavefront analysis device 4 serves to analyze the wavefront of the optical path in the eye. The topography analysis unit 5 serves to analyze the cornea surface of the eye. The means 7 for deriving the photo-ablation profile, which can also be designated as a calculation unit, has the task of calculating an appropriate ablation profile on the basis of the wavefront measured by the wavefront analysis device 4, on the basis of the topography measured by the topography analysis unit 5, and on the basis of the pupil diameter measured by the means 6 for measuring the photopic and mesopic pupil diameter. The data needed for this is supplied to the calculation unit 7 by the measuring units 4, 5 and 6 via suitable interfaces 9a, 9b and 9c. The calculation unit 7 also controls the actual ablation process.

The process and the appertaining device described here yield an ablation program that results in an improvement of the focal depth of the optically active zone of the cornea and thus to an improvement of the near vision. In contrast to the state of the art, this is attained in a way that the distance vision is not impaired. The distance vision remains refraction-neutral. Since moreover, according to the invention, two pupil sizes (light and dark) are taken into consideration, a more individual optimization is achieved. The additional introduction of transition zones contributes to the reduction of undesired side effects that are referred to as glare and halo (glare or halo after eye surgery means that the patient perceives a disturbing shining, flashing, brightness, aura or sparkling, for example, around sources of light). The creation of defined multifocality via the higher order of the spherical aberration prevents the sharp transitions of true bifocal zone divisions that evolve into undefined multifocality through later epithelial compensation.

LIST OF REFERENCE NUMERALS

1 device for the correction of visual inadequacies
2 laser system
3 beam modification device
4 wavefront analysis device
5 topography analysis unit
6 means for measuring the pupil diameter
7 calculation unit
8 laser beam
9a-9c interfaces
100-900 method steps

The invention claimed is:

1. A method for changing a property of an eye using a continuously multifocal profile that includes a component for increasing a focal depth, the method comprising:
   generating the continuously multifocal profile, wherein the generating includes calculating the component for increasing the focal depth to be rotation-symmetrical; and
   changing the property of the optical system according to the generated continuously multifocal profile, the changing of the property including at least one of performing ablation and changing a refractive property of the optical system.

2. The method as recited in claim 1, wherein the calculating the component for increasing the focal depth includes accounting for at least one of a photopic and a mesopic diameter of a pupil of the eye.

3. The method as recited in claim 1, wherein the profile results in a refractive power that is stronger in a central area of the optical system within the photopic diameter than in a peripheral, annular area between the photopic and mesopic diameters.

4. The method as recited in claim 1, wherein the calculating the component for increasing the focal depth includes optimizing an encircled energy criterion over an extended range of depth.

5. The method as recited in claim 4, wherein a diameter for the encircled energy criterion corresponds to an effective detector diameter of the optical system.

6. The method as recited in claim 1, wherein the profile additionally includes a component for correcting at least one of a myopia, a hyperopia and an astigmatism.

7. A method for changing a property of an eye using a continuously multifocal profile that includes a component for increasing a focal depth, the method comprising:
   generating the continuously multifocal profile, wherein the generating includes calculating the component for increasing the focal depth so as to optimize an encircled energy criterion over an extended range of depth; and
   changing the property of the optical system according to the generated continuously multifocal profile, the changing of the property including at least one of performing ablation and changing a refractive property of the optical system.

8. The method recited in claim 7, wherein a diameter for the encircled energy criterion corresponds to an effective detector diameter of the eye.

9. The method recited in claim 8, wherein the detector is a photoreceptor cell on a retina of the eye.

10. The method recited in claim 9, wherein the property of the eye is changed in such a way that an object detected by the eye in an area from a near vision to a distance vision are focused on the retina of the eye with a sufficient precision that an image is formed on the retina for each point of the detected object, and for the image, at least 90 percent of appertaining light beams are focused on the retina within a circle having a diameter that is not larger than that of the photoreceptor cell on the retina.

* * * * *